United States Patent
Gericke et al.

(10) Patent No.: US 7,405,239 B2
(45) Date of Patent: Jul. 29, 2008

(54) ACYLHYDRAZONE DERIVATIVES AND THE USE THEREOF IN THE INHIBITION, REGULATION AND/OR MODULATION OF KINASE SIGNAL TRANSDUCTION

(75) Inventors: Rolf Gericke, Seeheim-Jugenheim (DE); Norbert Beier, Reinheim (DE); Oliver Poeschke, Wiesbaden (DE); Lars Burgdorf, Frankfurt am Main (DE); Helga Drosdat, Heppenheim (DE); Florian Lang, Tübingen (DE)

(73) Assignee: Merck Patent GmbH, Darmstadt (DE)

( * ) Notice: Subject to any disclaimer, the term of this patent is extended or adjusted under 35 U.S.C. 154(b) by 20 days.

(21) Appl. No.: 10/574,781

(22) PCT Filed: Sep. 16, 2004

(86) PCT No.: PCT/EP2004/010398

§ 371 (c)(1),
(2), (4) Date: Apr. 6, 2006

(87) PCT Pub. No.: WO2005/037773

PCT Pub. Date: Apr. 28, 2005

(65) Prior Publication Data

US 2007/0060646 A1 Mar. 15, 2007

(30) Foreign Application Priority Data

Oct. 9, 2003 (DE) .................... 103 46 913

(51) Int. Cl.
*C07C 251/86* (2006.01)
*A61K 31/15* (2006.01)

(52) U.S. Cl. .................. 514/546; 514/563; 514/615; 560/136; 562/439; 564/148

(58) Field of Classification Search .......... 558/58; 562/439; 564/148; 514/563, 615
See application file for complete search history.

(56) References Cited

U.S. PATENT DOCUMENTS

| | | | |
|---|---|---|---|
| 2003/0225126 | A1 | 12/2003 | Markham et al. |
| 2004/0038882 | A1 | 2/2004 | Lang et al. |
| 2004/0110963 | A1 | 6/2004 | Burri et al. |

FOREIGN PATENT DOCUMENTS

| | | | |
|---|---|---|---|
| DE | 101 49 393 A1 | | 4/2003 |
| EP | 0 294 258 A1 | | 12/1988 |
| EP | 0 889 127 A1 | | 1/1999 |
| JP | 11-106371 | | 4/1999 |
| WO | WO 00/62781 A1 | | 10/2000 |
| WO | WO-01/70213 | * | 9/2001 |
| WO | WO 01/70213 A2 | | 9/2001 |
| WO | WO 02/17893 A2 | | 3/2002 |
| WO | WO 02/070464 A2 | | 9/2002 |
| WO | WO 02/074987 A2 | | 9/2002 |

OTHER PUBLICATIONS

Dilanyan et al., Chemical Abstracts, 125:212091, 1996.*
Kotali et al., Chemical Abstracts, 125:275360, 1996.*
Pandeya et al., Acta Pharmaceutica (Zagreb, Croatia), 53(1), 15-24, 2003.*
Muanprasat et al., Journal of General Physiology, 124(2), 125-137, Aug. 2004.*
Pandeya et al., Pharmazie, 56(2), 121-124, 2001.*
Issa et al., Synthesis and Reactivity in Inorganic and Metal-Organic Chemistry, 31(1), 95-105, 2001.*
XP-001205216; Pandeya et al.; "Design of semicarbazones and their bio-isosteric analogues as potential anticonvulsants"; Pharmazie vol. 56, 2001; pp. 121-125.
XP-002316513; Chemcats—ChemStar Product List; Apr. 2003: pp.1-4; accession No. 2000:911593.
XP-002316522; Beilstein Registry #3324432; Beilstein Institut zur Foerderung der Chemischen Wissenschaften; 1988-2003; pp. 1-2.
XP-002316521; Beilstein Registry #2381518; Beilstein Institut zur Foerderung der Chemischen Wissenschaften; 1988-2003; pp. 1.
XP-002316520; Beilstein Registry #3365109; Beilstein Institut zur Foerderung der Chemischen Wissenschaften; 1988-2003; pp. 1.

(Continued)

*Primary Examiner*—Fiona T Powers
(74) *Attorney, Agent, or Firm*—Millen, White, Zelano, Branigan, P.C.

(57) ABSTRACT

The invention relates to acylhydrazone derivatives of formula (I), which are SGK inhibitors and can be used for the treatment of diseases and afflictions associated with SGK, such as diabetes, obesity, metabolic syndrome (dyslipidaemia), systematic and pulmonary hypertension, cardiovascular diseases and kidney diseases and in general for all types of fibroses and inflammatory processes. In said formula: $R^1$ and $R^5$ independently of one another represent H, OH, OA, OAc or methyl; $R^2$, $R^3$, $R^4$, $R^6$, $R^7$, $R^8$, $R^9$ and $R^{10}$ independently of one another represent H, OH, OA, OAc, $OCF_3$, Hal, $NO_2$, $CF_3$, A, CN, $OSO_2CH_3$, $SO_2CH_3$, $NH_2$, or COOH; $R^{11}$ represents H or $CH_3$; A represents an alkyl comprising 1, 2, 3, or 4 C atoms; X represents $CH_2$, $CH_2CH_2$, $OCH_2$ or —CH(OH)— and Hal represents F, Cl, Br or I.

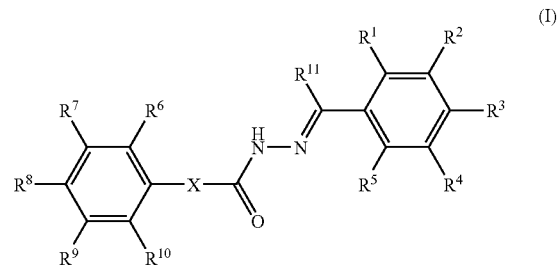

(I)

5 Claims, No Drawings

OTHER PUBLICATIONS

XP-002316519; STN CA Caesar accession No. 1165; pp. 1.
XP-002316518; STN CA Caesar accession No. 1135; pp. 1.
XP-002316517; STN CA Caesar accession No. 1163; pp. 1.
XP-002316516; STN CA Caesar accession No. 1142; pp. 1-2.
XP-002316515; STN CA Caesar accession No. 1167; pp. 1-2.
XP-002316514; 1/6—(c) File Chemcats; accession No. 2001:2460460; pp. 1-4.

* cited by examiner

ACYLHYDRAZONE DERIVATIVES AND THE USE THEREOF IN THE INHIBITION, REGULATION AND/OR MODULATION OF KINASE SIGNAL TRANSDUCTION

BACKGROUND OF THE INVENTION

The invention had the object of finding novel compounds having valuable properties, in particular those which can be used for the preparation of medicaments.

The present invention relates to compounds in which the inhibition, regulation and/or modulation of kinase signal transduction, in particular by the cell volume-regulated human kinase h-sgk (human serum and glucocorticoid dependent kinase or SGK), plays a role, furthermore to pharmaceutical compositions which comprise these compounds, and to the use of the compounds for the treatment of SGK-induced diseases.

The SGKs having the isoforms SGK-1, SGK-2 and SGK-3 are a serine/threonine protein kinase family (WO 02/17893). The compounds according to the invention are preferably selective inhibitors of SGK-1. They may furthermore be inhibitors of SGK-2 and/or SGK-3.

In detail, the present invention relates to compounds which inhibit, regulate and/or modulate signal transduction by SGKs, to compositions which comprise these compounds, and to processes for the use thereof for the treatment of SGK-induced diseases and conditions, such as diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardial fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), generally in any type of fibrosis and inflammatory process (for example liver cirrhosis, pulmonary fibrosis, fibrosing pancreatitis, rheumatism and arthritis, Crohn's disease, chronic bronchitis, radiation fibrosis, sclerodermatitis, cystic fibrosis, scarring, Alzheimer's disease).

The compounds according to the invention can also inhibit the growth of tumour cells and tumour metastases and are therefore suitable for tumour therapy.

The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immunocoagulopathy or complex coagulopathies, and also in neuronal excitability, for example epilepsy. The compounds according to the invention can also be employed therapeutically in the treatment of a glaucoma or cataract.

The compounds according to the invention are furthermore used in the treatment of bacterial infections and in antiinfection therapy. The compounds according to the invention can also be employed therapeutically for increasing learning ability and attention.

The identification of small compounds which specifically inhibit, regulate and/or modulate signal transduction of SGKs is therefore desirable and an aim of the present invention.

It has been found that the compounds according to the invention and salts thereof have very valuable pharmacological properties while being well tolerated.

In particular, they exhibit inhibiting properties on SGK.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and also to a process for the treatment of the said diseases which comprises the administration of one or more compounds according to the invention to a patient in need of such an administration.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

The susceptibility of a certain cell to treatment with the compounds according to the invention can be determined by in-vitro tests. Typically, a culture of the cell is combined with a compound according to the invention at various concentrations for a period of time which is sufficient to enable the active agents to induce cell death or inhibit migration, usually between approximately one hour and one week. For testing in vitro, use can be made of cultivated cells from a biopsy sample. The viable cells remaining after the treatment are then counted.

The dose varies depending on the specific compound used, the specific disease, the patient status, etc. A therapeutic dose is typically sufficient in order considerably to reduce the undesired cell population in the target tissue, while the viability of the patient is maintained. The treatment is generally continued until a considerable reduction has occurred, for example at least an approx. 50% reduction in the cell burden, and can be continued until undesired cells are essentially no longer detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

Various assay systems are available for identification of kinase inhibitors. In the scintillation proximity assay (Sorg et al., J. of Biomolecular Screening, 2002, 7, 11-19) and the flashplate assay, the radioactive phosphorylation of a protein or peptide as substrate using γATP is measured. In the presence of an inhibitory compound, a reduced radioactive signal, or none at all, is detectable. Furthermore, homogeneous time-resolved fluorescence resonance energy transfer (HTR-FRET) and fluorescence polarisation (FP) technologies are useful as assay methods (Sills et al., J. of Biomolecular Screening, 2002, 191-214).

Other non-radioactive ELISA assay methods use specific phospho antibodies (phospho ABs). The phospho AB only binds the phosphorylated substrate. This binding can be detected by chemoluminescence using a second peroxidase-conjugated antisheep antibody (Ross et al., Biochem. J., 2002, 366, 977-981).

PRIOR ART

WO 00/62781 describes the use of medicaments comprising inhibitors of the cell volume-regulated human kinase H-SGK.

Benzylidenebenzohydrazides having an antibacterial action are described in WO 02/070464 A2. The use of acyl hydrazides for the treatment of bacterial infections is disclosed in WO 01/70213.

Other acylhydrazone derivatives, inter alia for the treatment of diabetes complications, are disclosed in JP 11-106371.

Methoxy-substituted aromatic acylhydrazone derivatives for the treatment of cancer are described by T. Kametani et al. in Yakugaku Zasshi (1963), 83, 851-855 and in Yakugaku Zasshi (1963), 83, 844-847.

Other aromatic acylhydrazone derivatives as sedative enhancers and for lowering the blood pressure are disclosed in JP 41-20699.

The use of kinase inhibitors in antiinfection therapy is described by C. Doerig in Cell. Mol. Biol. Lett. Vol. 8, No. 2A, 2003, 524-525.

The use of kinase inhibitors in obesity is described by N. Perrotti in J. Biol. Chem. Mar. 23, 2001; 276(12):9406-9412.

The following references suggest and/or describe the use of SGK inhibitors in cancer treatment:

1: Chung E J, Sung Y K, Farooq M, Kim Y, Im S, Tak W Y, Hwang Y J, Kim Y I, Han H S, Kim J C, Kim M K. Gene expression profile analysis in human hepatocellular carcinoma by cDNA microarray. Mol Cells. 2002; 14:382-7.
2: Brickley D R, Mikosz C A, Hagan C R, Conzen S D. Ubiquitin modification of serum and glucocorticoid-induced protein kinase-1(SGK-1). J Biol. Chem. 2002; 277: 43064-70.
3: Fillon S, Klingel K, Warntges S, Sauter M, Gabrysch S, Pestel S, Tanneur V, Waldegger S, Zipfel A, Viebahn R, Haussinger D, Broer S, Kandolf R, Lang F. Expression of the serine/threonine kinase hSGK1 in chronic viral hepatitis. Cell Physiol Biochem. 2002; 12:47-54.
4: Brunet A, Park J, Tran H, Hu L S, Hemmings B A, Greenberg M E. Protein kinase SGK mediates survival signals by phosphorylating the forkhead transcription factor FKHRL1 (FOXO3a). Mol Cell Biol 2001; 21:952-65
5: Mikosz C A, Brickley D R, Sharkey M S, Moran T W, Conzen S D. Glucocorticoid receptor-mediated protection from apoptosis is associated with induction of the serine/threonine survival kinase gene, sgk-1. J Biol. Chem. 2001; 276:16649-54.
6: Zuo Z, Urban G, Scammell J G, Dean N M, McLean T K, Aragon I, Honkanen R E. Ser/Thr protein phosphatase type 5 (PP5) is a negative regulator of glucocorticoid receptor-mediated growth arrest. Biochemistry. 1999; 38:8849-57.
7: Buse P, Tran S H, Luther E, Phu P T, Aponte G W, Firestone G L. Cell cycle and hormonal control of nuclear-cytoplasmic localisation of the serum- and glucocorticoid-inducible protein kinase, Sgk, in mammary tumour cells. A novel convergence point of anti-proliferative and proliferative cell signalling pathways. J Biol. Chem. 1999; 274:7253-63.

SUMMARY OF THE INVENTION

The invention relates to compounds of the formula I

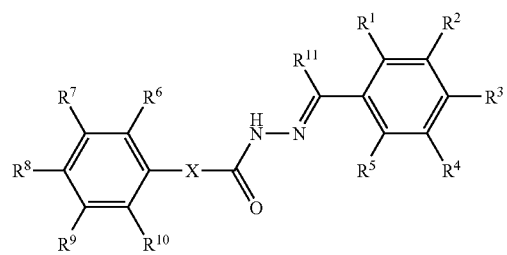

in which
$R^1$, $R^5$ each, independently of one another, denote H, OH, OA, OAc or methyl,
$R^2$, $R^3$, $R^4$, $R^6$, $R^7$, $R^8$, $R^9$, $R^{10}$ each, independently of one another, denote H, OH, OA, OAc, OCF$_3$, Hal, NO$_2$, CF$_3$, A, CN, OSO$_2$CH$_3$, SO$_2$CH$_3$, NH$_2$ or COOH,
$R^{11}$ denotes H or CH$_3$,
A denotes alkyl having 1, 2, 3 or 4 C atoms,
X denotes CH$_2$, CH$_2$CH$_2$, OCH$_2$ or —CH(OH)—,
Hal denotes F, Cl, Br or I, and pharmaceutically usable derivatives, salts, solvates and stereoisomers thereof, including mixtures thereof in all ratios.

Particular preference is given to compounds of the formula I in which
$R^1$ denotes methyl, OA or OH,
$R^5$ denotes H or methyl,
$R^2$ denotes H, NO$_2$ or Hal,
$R^4$ denotes H or Hal,
$R^3$ denotes OH or OAc,
$R^6$ denotes H,
$R^7$ denotes OA, H, Hal, OH, CF$_3$ or NO$_2$,
$R^8$ denotes H, OH or Hal,
$R^9$ denotes H, A, Hal, OSO$_2$CH$_3$ or OH,
$R^{10}$ denotes H, A or Hal,
$R^{11}$ denotes H or CH$_3$,
A denotes alkyl having 1, 2, 3 or 4 C atoms,
X denotes CH$_2$, CH$_2$CH$_2$, OCH$_2$ or —CH(OH)—,
Hal denotes F, Cl, Br or I, and pharmaceutically usable derivatives, salts, solvates and stereoisomers thereof, including mixtures thereof in all ratios.

Very particular preference is given to compounds of the formula I in which
$R^1$ denotes OH, OCH$_3$ or CH$_3$,
$R^5$ denotes H,
$R^2$ denotes H,
$R^4$ denotes H,
$R^3$ denotes OH,
$R^6$ denotes H,
$R^7$ denotes OH,
$R^8$ denotes H, OH or Hal,
$R^9$ denotes H, A, Hal, OSO$_2$CH$_3$ or OH,
$R^{10}$ denotes H, A or Hal,
$R^{11}$ denotes H or CH$_3$,
A denotes alkyl having 1, 2, 3 or 4 C atoms,
X denotes CH$_2$, CH$_2$CH$_2$, OCH$_2$ or —CH(OH)—,
Hal denotes F, Cl, Br or I, and pharmaceutically usable derivatives, salts, solvates and stereoisomers thereof, including mixtures thereof in all ratios.

Particular preference is furthermore given to compounds of the formula I in which
R$^1$ denotes H, methyl, OA, OAc or OH,
R$^5$ denotes H, methyl or OA,
R$^2$ denotes H, NO$_2$, Hal OA, A or COOH,
R$^4$ denotes H, Hal, A, CF$_3$, NO$_2$ or OA
R$^3$ denotes OH, OAc, SO$_2$CH$_3$, Hal, CF$_3$, OCF$_3$, COOH, OA, H, A or NO$_2$,
R denotes H, A or OA,
R$^7$ denotes OA, H, Hal, OH, CF$_3$, NO$_2$ or NH$_2$,
R$^8$ denotes H, OH, OA or Hal,
R$^9$ denotes H, A, Hal, OSO$_2$CH$_3$ or OH,
R$^{10}$ denotes H, A, OA or Hal,
R$^{11}$ denotes H or CH$_3$,
A denotes alkyl having 1, 2, 3 or 4 C atoms,
X denotes CH$_2$, CH$_2$CH$_2$, OCH$_2$ or —CH(OH)—,
Hal denotes F, Cl, Br or I, and pharmaceutically usable derivatives, salts, solvates and stereoisomers thereof, including mixtures thereof in all ratios.

The invention relates, in particular, to compounds selected from the group of the acylhydrazone derivatives
N-(4-hydroxy-2-methoxybenzylidene)-(3-hydroxyphenyl)acetohydrazide,
N-[1-(4-hydroxy-2-methoxyphenyl)ethylidene]-(3-hydroxyphenyl)acetohydrazide,
N-(4-hydroxy-2-methoxybenzylidene)-(3-methoxyphenyl)acetohydrazide,
N-(3-fluoro-4-hydroxybenzylidene)phenylacetohydrazide,
N-(4-hydroxy-2-methoxybenzylidene)-(4-hydroxyphenyl)acetohydrazide,
N-(4-hydroxy-2-methoxybenzylidene)-(3,4-dichlorophenyl)acetohydrazide,
N-(4-hydroxy-2-methoxybenzylidene)-m-tolylacetohydrazide,
N-(4-hydroxy-2-methoxybenzylidene)-o-tolylacetohydrazide,
N-(4-hydroxy-2-methoxybenzylidene)-(2-chlorophenyl)acetohydrazide,
N-(4-hydroxy-2-methoxybenzylidene)-(3-chlorophenyl)acetohydrazide,
N-(4-hydroxy-2-methoxybenzylidene)-(4-fluorophenyl)acetohydrazide,
N-(4-hydroxy-2-methoxybenzylidene)-(2-chloro-4-fluorophenyl)acetohydrazide,
N-(4-hydroxy-2-methoxybenzylidene)-(3-fluorophenyl)acetohydrazide,
N-(4-hydroxybenzylidene)-(3-methoxyphenyl)acetohydrazide,
N-(4-hydroxy-2,6-dimethylbenzylidene)-(3-methoxyphenyl)acetohydrazide,
N-(3-fluoro-4-hydroxybenzylidene)-(3-methoxyphenyl)acetohydrazide,
N-[1-(4-hydroxy-2-methoxyphenyl)ethylidene]-(3-methoxyphenyl)acetohydrazide,
N-(4-hydroxy-2-methoxybenzylidene)-(3-methylsulfonyloxyphenyl)acetohydrazide,
N-(4-hydroxy-2-methoxybenzylidene)-(3,5-dihydroxyphenyl)acetohydrazide,
N-(3-fluoro-4-hydroxybenzylidene)-(3-fluorophenyl)acetohydrazide,
N-(4-acetoxy-2-methoxybenzylidene)-(3-methoxyphenyl)acetohydrazide,
N-(4-hydroxy-2-methoxybenzylidene)-(3-trifluoromethylphenyl)acetohydrazide,
N-(4-hydroxy-2-methoxybenzylidene)-3-(3-methoxyphenyl)propiohydrazide,
N-(2,4-dihydroxybenzylidene)-(3-methoxyphenyl)acetohydrazide,
N-(4-hydroxy-2-methoxybenzylidene)-(3-methoxyphenoxy)acetohydrazide,
N-(4-hydroxy-2-methoxybenzylidene)-(3-nitrophenyl)acetohydrazide,
N-(5-chloro-2-hydroxybenzylidene)-(3-methoxyphenyl)acetohydrazide,
N-(2-hydroxy-5-nitrobenzylidene)-(3-methoxyphenyl)acetohydrazide,
N-(4-hydroxy-2-methoxybenzylidene)-2-hydroxy-2-phenylacetohydrazide,
N-(2-ethoxy-4-hydroxybenzylidene)-(3-methoxyphenyl)acetohydrazide,
N-(4-hydroxy-2-methoxybenzylidene)-(3-bromophenyl)acetohydrazide,
N-[1-(4-hydroxyphenyl)ethylidene]-(3-methoxyphenyl)acetohydrazide,
N-(4-hydroxy-2-methoxybenzylidene)-(3,5-difluorophenyl)acetohydrazide,
N-(4-hydroxy-2-methylbenzylidene)-(3-hydroxyphenyl)acetohydrazide,
N-(2-ethoxy-4-hydroxybenzylidene)-(3-hydroxyphenyl)acetohydrazide,
N-(2-methoxy-4-hydroxy-6-methylbenzylidene)-(3-hydroxyphenyl)acetohydrazide,
N-(2-methoxy-4-hydroxybenzylidene)-(2-fluorophenyl)acetohydrazide, and pharmaceutically usable derivatives, salts, solvates and stereoisomers thereof, including mixtures thereof in all ratios.

The invention also relates to the stereoisomers (E, Z isomers) and the hydrates and solvates of these compounds. Solvates of the compounds are taken to mean adductions of inert solvent molecules onto the compounds which form owing to their mutual attractive force. Solvates are, for example, mono- or dihydrates or alcoholates.

The compounds according to the invention are preferably in the E configuration.

Pharmaceutically usable derivatives is taken to mean, for example, the salts of the compounds according to the invention and also so-called prodrug compounds.

Prodrug derivatives is taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as is described, for example, in Int. J. Pharm. 115, 61-67 (1995).

The expression "effective amount" means the amount of a medicament or pharmaceutical active ingredient which causes a biological or medical response which is sought or aimed at, for example by a researcher or physician, in a tissue, system, animal or human.

In addition, the expression "therapeutically effective amount" means an amount which, compared with a corresponding subject who has not received this amount, has the following consequence: improved treatment, healing, prevention or elimination of a disease, syndrome, condition, complaint, disorder or side effects or also the reduction in the progress of a disease, condition or disorder.

The expression "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

A denotes alkyl, is unbranched (linear) or branched, and has 1, 2, 3 or 4 C atoms. A preferably denotes methyl, furthermore ethyl, propyl, isopropyl, butyl, isobutyl, sec-butyl or tert-butyl.

Ac denotes acyl having 1-6 C atoms, preferably formyl, acetyl or propionyl.

X preferably denotes $CH_2$.

$R^1$ preferably denotes H, methyl, OA or OH, particularly preferably OH, $OCH_3$ or methyl.

$R^5$ preferably denotes H or methyl, particularly preferably H.

$R^2$ preferably denotes H, $NO_2$ or Hal, particularly preferably H.

$R^4$ preferably denotes H or Hal, particularly preferably H.

$R^3$ preferably denotes OH or OAc, particularly preferably OH.

$R^6$ preferably denotes H.

$R^7$ preferably denotes OA, H, Hal, OH, $CF_3$ or $NO_2$, particularly preferably OH.

$R^8$ preferably denotes H, OH or Hal.

$R^9$ preferably denotes H, A, Hal or OH.

$R^{10}$ preferably denotes H, A or Hal.

The compounds according to the invention and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned in greater detail here.

If desired, the starting materials can also be formed in situ so that they are not isolated from the reaction mixture, but instead are immediately converted further into the compounds according to the invention.

The starting compounds are generally known. If they are novel, they can, however, be prepared by methods known per se.

Compounds of the formula I can preferably be obtained by reacting a hydrazide with an aldehyde or ketone.

In the case of reaction with a ketone (see Example 2), a mixture of (E, Z) stereoisomers, which can be separated, is generally formed.

The reaction is carried out by methods known to the person skilled in the art.

The reaction is firstly carried out in a suitable solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The solvents are particularly preferably alcohols, such as, for example, isopropanol or ethanol.

Depending on the conditions used, the reaction time is between a few minutes and 14 days, the reaction temperature is between about −30° and 140°, normally between −10° and 110°, in particular between about 20° and about 100°.

A base of the compounds of the formula I according to the invention can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds according to the invention.

On the other hand, compounds of the formula I can be converted into the corresponding metal salts, in particular alkali metal or alkaline-earth metal salts, using bases (for example sodium hydroxide or carbonate or potassium hydroxide or carbonate) or into the corresponding ammonium.

It is also possible to use physiologically acceptable organic bases, such as, for example, ethanolamine.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl pyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in the freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the animal, the precise disease condition which requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg would usually be between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as a fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound according to the invention and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, in particular for humans, in the treatment of SGK-induced diseases.

The invention thus relates to the use of compounds according to Claim 1 and pharmaceutically usable derivatives, solvates and stereoisomers thereof, including mixtures thereof in all ratios, for the preparation of a medicament for the treatment of diseases in which the inhibition, regulation and/or modulation of signal transduction by kinases plays a role. Preference is given here to SGK.

Preference is given to the use of compounds according to Claim 1 and pharmaceutically usable derivatives, solvates and stereoisomers thereof, including mixtures thereof in all ratios, for the preparation of a medicament for the treatment of diseases which are influenced by inhibition of SGKs by the compounds according to Claim 1.

The present invention encompasses the use of the compounds according to Claim 1 according to the invention and/or physiologically acceptable salts and solvates thereof for the preparation of a medicament for the treatment or prevention of diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardial fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), generally in any type of fibrosis and inflammatory process (for example liver cirrhosis, pulmonary fibrosis, fibrosing pancreatitis, rheumatism and arthrosis, Crohn's disease, chronic bronchitis, radiation fibrosis, sclerodermatitis, cystic fibrosis, scarring, Alzheimer's disease).

The compounds according to the invention can also inhibit the growth of cancer, tumour cells and tumour metastases and are therefore suitable for tumour therapy.

The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immunocoagulopathy or complex coagulopathies, and also in neuronal excitability, for example epilepsy. The compounds according to the invention can also be employed therapeutically in the treatment of glaucoma or a cataract. The compounds according to the invention are furthermore used in the treatment of bacterial infections and in antiinfection therapy. The compounds according to the invention can also be employed therapeutically for increasing learning ability and attention.

Preference is given to the use of compounds according to Claim 1 and pharmaceutically usable derivatives, solvates and stereoisomers thereof, including mixtures thereof in all ratios, for the preparation of a medicament for the treatment or prevention of diabetes, obesity, metabolic syndrome (dyslipidaemia), systemic and pulmonary hypertonia, cardiovascular diseases and renal diseases, generally in any type of fibrosis and inflammatory process, cancer, tumour cells, tumour metastases, coagulopathies, neuronal excitability, glaucoma, cataract, bacterial infections and in antiinfection therapy, for increasing learning ability and attention.

Diabetes is preferably diabetes mellitus, diabetic nephropathy, diabetic neuropathy, diabetic angiopathy and microangiopathy.

Cardiovascular diseases are preferably cardial fibroses after myocardial infarction, cardiac hypertrophy, cardiac insufficiency and arteriosclerosis.

Renal diseases are preferably glomerulosclerosis, nephrosclerosis, nephritis, nephropathy and electrolyte excretion disorder.

Fibroses and inflammatory processes are preferably liver cirrhosis, pulmonary fibrosis, fibrosing pancreatitis, rheumatism and arthrosis, Crohn's disease, chronic bronchitis, radiation fibrosis, sclerodermatitis, cystic fibrosis, scarring, Alzheimer's disease.

Assays

The compounds according to the invention described in the examples were tested in the assays described below and were found to have kinase-inhibitory activity. Further assays are known from the literature and could easily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

Above and below, all temperatures are indicated in ° C. In the following examples, "conventional work-up" means: if necessary, water is added, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) M+
FAB (fast atom bombardment) (M+H)+
ESI (electrospray ionisation) (M+H)+ (unless indicated otherwise)

EXAMPLE 1

The preparation of N-(4-hydroxy-2-methoxybenzylidene)-(3-hydroxyphenyl)acetohydrazide ("1") is carried out analogously to the following scheme:

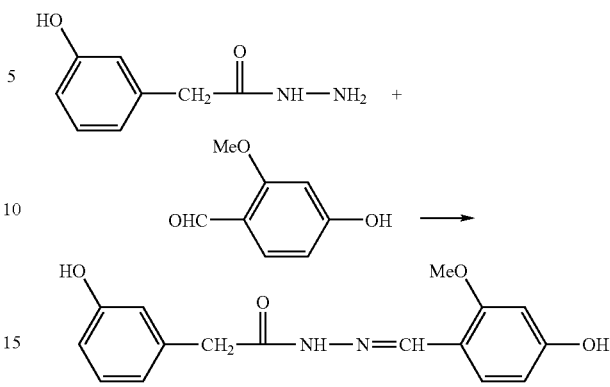

4-Hydroxy-2-methoxybenzaldehyde (5.5 g) and (3-hydroxyphenyl)acetohydrazide (6 g) are heated under reflux for 2 h in 200 ml of i-PrOH. The mixture is stirred at RT for a further hour. The crystals which precipitate during this time are filtered off with suction and recrystallised from MeCN.

Yield: 8.13 g (75%); m.p. 205° C.

EXAMPLE 2

The preparation of N-[1-(4-hydroxy-2-methoxyphenyl)ethylidene]-(3-hydroxyphenyl)acetohydrazide ("2", "3") is carried out analogously to the following scheme:

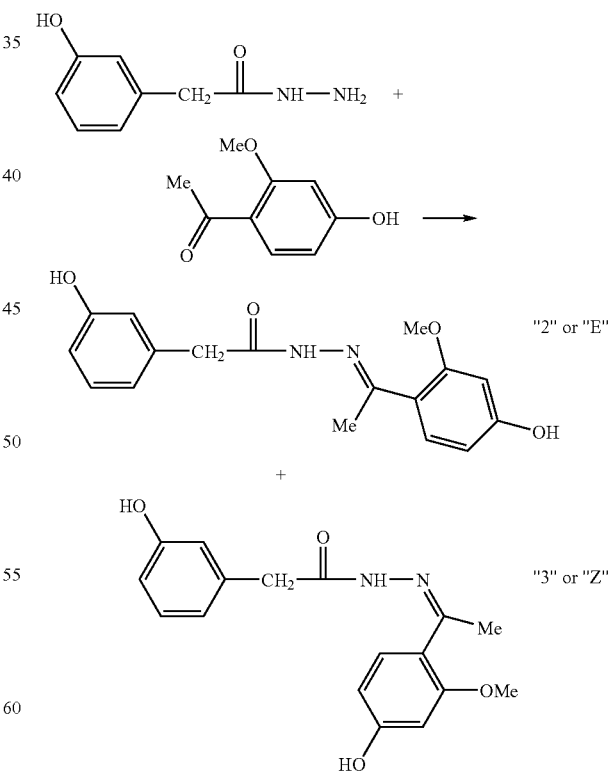

1-(4-Hydroxy-2-methoxyphenyl)ethanone (680 mg) and (3-hydroxyphenyl)acetohydrazide (665 mg) are heated at 70° C. for 4 days in 15 ml of EtOH. The solvent is removed, and the residue is chromatographed over silica gel. The uniform fractions are combined, the solvent is stripped off and crystallised using MeCN.

Yield: nonpolar substance "2" (E configuration was determined by means of 2D-NMR) 120 mg (9%), m.p. 142°, and polar substance "3" (Z configuration was determined by means of 2D-NMR) 50 mg (4%), m.p. 180°.

The following compounds are obtained analogously to Example 1 or 2

| No. | Structural formula | M.p. [° C.] |
|---|---|---|
| 4 | | 166-167 |
| 5 | | 207 |
| 6 | | 224 |
| 7 | | 232-233 |
| 8 | | 207-208 |
| 9 | | 119-120 |
| 10 | | 134-135 |

-continued
| No. | Structural formula | M.p. [° C.] |
|---|---|---|
| 11 | 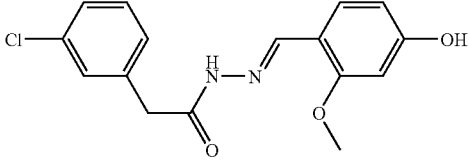 | 121-122 |
| 12 | 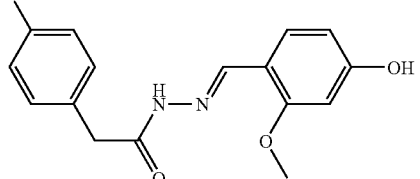 | 184-185 |
| 13 | 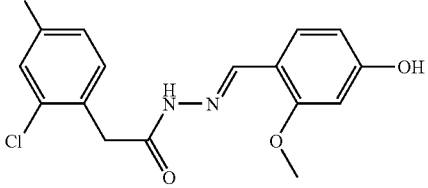 | 242-243 |
| 14 | 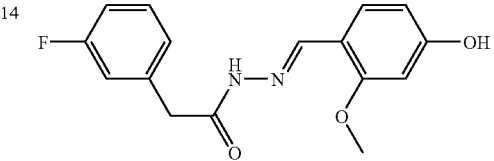 | 111-112 |
| 15 | 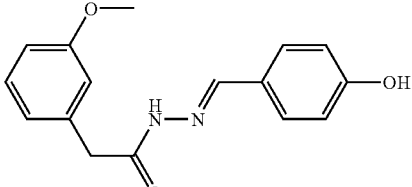 | 162-163 |
| 16 | 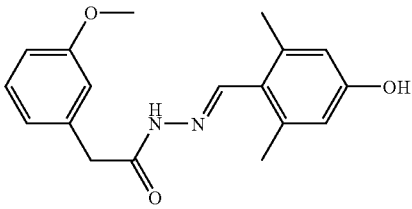 | 172-173 |
| 17 | 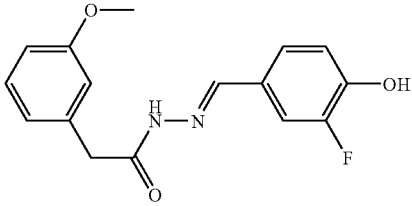 | 190-191 |

-continued

| No. | Structural formula | M.p. [° C.] |
| --- | --- | --- |
| 18 | | 160-162 |
| 19 | | 246 (decomposition) |
| 20 | | 193-194 |
| 21 | | 147-148 |
| 22 | | 203-204 |
| 23 | | 159-160 |
| 24 | | 205-206 |

-continued

| No. | Structural formula | M.p. [° C.] |
|---|---|---|
| 25 | | 173-174 |
| 26 | | 240-241 |
| 28 | | 178-179 |
| 29 | | 198-199 |
| 30 | | 217-218 |
| 31 | | |

-continued

| No. | Structural formula | M.p. [° C.] |
|---|---|---|
| 33 | | 214-215 |
| 34 | | 162-164 |
| 35 | | 132 |
| 36 | | 224-225 |
| 37 | | 203-204 |
| 38 | | 190-192 |
| 40 | | 194-195 |

| No. | Structural formula | M.p. [° C.] |
|---|---|---|
| 41 | 2-fluorophenyl-CH₂-C(=O)-NH-N=CH-(4-hydroxy-2-methoxyphenyl) | 213-215 |

The following compounds are obtained analogously to Example 1 or 2

N-(2,4-dihydroxybenzylidene)-(3-hydroxyphenyl)acetohydrazide (42), m.p. 181-183;
N-(2-hydroxy-5-chlorobenzylidene)-(3-hydroxyphenyl)acetohydrazide (43), m.p. 196-197;
N-(4-methylsulfonylbenzylidene)-(3-hydroxyphenyl)acetohydrazide (44), m.p. 196-197;
N-(2,6-dimethyl-4-hydroxybenzylidene)-(3-hydroxyphenyl)acetohydrazide (45), m.p. 208-209;
N-(2-methoxy-4-hydroxybenzylidene)-(3-hydroxy-4-methoxyphenyl)acetohydrazide (46), m.p. 239-240;
N-(2-methoxy-4-hydroxybenzylidene)-(2,3-dimethoxyphenyl)acetohydrazide (47), m.p. 192-193;
N-(2-methoxy-4-hydroxybenzylidene)-(3-aminophenyl)acetohydrazide (48), m.p. 210-211;
N-(2,4-dihydroxy-6-methylbenzylidene)-(3-hydroxyphenyl)acetohydrazide (49), m.p. 222-230;
N-(2-methoxy-4-hydroxybenzylidene)-(2-methyl-3-methoxyphenyl)acetohydrazide (50), m.p. 205-207;
N-(4-bromobenzylidene)-(3-hydroxyphenyl)acetohydrazide (51), m. p. 216-217;
N-(4-iodobenzylidene)-(3-hydroxyphenyl)acetohydrazide (52), m. p. 229-230;
N-(2-hydroxy-3-bromo-5-chlorobenzylidene)-(3-hydroxyphenyl)acetohydrazide (53), m.p. 208-209;
N-(2-hydroxy-5-tert-butylbenzylidene)-(3-hydroxyphenyl)acetohydrazide (54), m.p. 162-163;
N-(2-hydroxy-5-bromobenzylidene)-(3-hydroxyphenyl)acetohydrazide (55), m.p. 209-210;
N-(2-hydroxy-5-trifluoromethoxybenzylidene)-(3-hydroxyphenyl)acetohydrazide (56), m.p. 184;
N-(2-hydroxy-3-methoxy-5-nitrobenzylidene)-(3-hydroxyphenyl)acetohydrazide (57), m.p. 153-154;
N-(4-hydroxybenzylidene)-(3-hydroxyphenyl)acetohydrazide (58), m.p. 186-187;
N-(4-hydroxy-2-methoxybenzylidene)-(3-ethoxyphenyl)acetohydrazide (59), m.p. 176-177;
N-(2-hydroxy-3,5-dichlorobenzylidene)-(3-hydroxyphenyl)acetohydrazide (60), m.p. 205-206;
N-(2-hydroxy-5-iodobenzylidene)-(3-hydroxyphenyl)acetohydrazide (61), m.p. 216-217,
N-(2-hydroxy-5-nitrobenzylidene)-(3-hydroxyphenyl)acetohydrazide (62), from about 200° slow decomposition;
N-(2-hydroxy-3-methyl-5-chlorobenzylidene)-(3-hydroxyphenyl)acetohydrazide (63), m.p. 207-208;
N-(2-hydroxy-5-fluorobenzylidene)-(3-hydroxyphenyl)acetohydrazide (64), m.p. 217-218;
N-(2-hydroxy-6-methylbenzylidene)-(3,5-difluorophenyl)acetohydrazide (65), m.p. 247-248;
N-(2-hydroxy-6-methylbenzylidene)-(3-fluorophenyl)acetohydrazide (66), m.p. 251-252;
N-(2-hydroxy-6-methylbenzylidene)phenyl acetohydrazide (67), m.p. 239-240;
N-[1-(4-hydroxyphenyl)ethylidene]-(3-hydroxyphenyl)acetohydrazide (68), m.p. 202-204;
N-[1-(2,4-dihydroxyphenyl)ethylidene]-(3-hydroxyphenyl)acetohydrazide (69), m.p. 174;
N-(2,4-dihydroxy-6-methylbenzylidene)-(3-methyl-5-methoxyphenyl)acetohydrazide (70), m.p. 217-219;
N-(2,4-dihydroxy-6-methylbenzylidene)-(3,5-dihydroxyphenyl)acetohydrazide (71), from about 278° slow decomposition;
N-(2-hydroxy-4-carboxybenzylidene)-(3-hydroxyphenyl)acetohydrazide (72), m.p. 330;
N-(2,3-dimethyl-4-hydroxybenzylidene)-(3-hydroxyphenyl)acetohydrazide (73), m.p. 226-228;
N-(3,5-di-tert-butyl-4-hydroxybenzylidene)-(3-hydroxyphenyl)acetohydrazide (74), m.p. 238-239;
N-(3,5-dimethyl-4-hydroxybenzylidene)-(3-hydroxyphenyl)acetohydrazide (75), m.p. 224;
N-(2-acetoxybenzylidene)-(3-hydroxyphenyl)acetohydrazide (76), m.p. 125-126;
N-(2-hydroxybenzylidene)-(3-hydroxyphenyl)acetohydrazide (77), m.p. 188-189;
N-(2-hydroxy-3-methoxybenzylidene)-(3-hydroxyphenyl)acetohydrazide (78), m.p. 185;
N-(2-hydroxy-5-methoxybenzylidene)-(3-hydroxyphenyl)acetohydrazide (79), m.p. 180;
N-(2-hydroxy-5-nitrobenzylidene)-(3-hydroxyphenyl)acetohydrazide (80), m.p. 229-230;
N-(2-hydroxy-3-methylbenzylidene)-(3-hydroxyphenyl)acetohydrazide (81), m.p. 204-205;
N-(2-hydroxy-3-nitrobenzylidene)-(3-hydroxyphenyl)acetohydrazide (82), m.p. 183;
N-(2-hydroxy-6-methoxybenzylidene)-(3-hydroxyphenyl)acetohydrazide (83), m.p. 192-193;
N-(2-hydroxy-5-methylbenzylidene)-(3-hydroxyphenyl)acetohydrazide (84), m.p. 205-206;
N-(3-bromobenzylidene)-(3-hydroxyphenyl)acetohydrazide (85), m.p. 226-227;
N-(2-hydroxy-3-tert-butylbenzylidene)-(3-hydroxyphenyl)acetohydrazide (86), m.p. 189-190;
N-(2-hydroxy-4-methylbenzylidene)-(3-hydroxyphenyl)acetohydrazide (87), m.p. 191-192;
N-(2-hydroxy-3-nitro-5-bromobenzylidene)-(3-hydroxyphenyl)acetohydrazide (88), m.p. 240-241;
N-(2-hydroxy-4-methyl-5-chlorobenzylidene)-(3-hydroxyphenyl)acetohydrazide (89), m.p. 232-234;
N-(2,6-dimethoxybenzylidene)-(3-hydroxyphenyl)acetohydrazide (90), m.p. 181;
N-(2-hydroxy-3-fluorobenzylidene)-(3-hydroxyphenyl)acetohydrazide (91), m.p. 160-161;
N-(2-hydroxy-3-bromo-5-nitrobenzylidene)-(3-hydroxyphenyl)acetohydrazide (92), m.p. 214-241.5;
N-(2-hydroxy-6-methylbenzylidene)-(3-hydroxyphenyl)acetohydrazide (93), m.p. 198;

N-(2-hydroxy-4-methoxy-6-methylbenzylidene)-(3-hydroxyphenyl)acetohydrazide (94), m.p. 192;
N-(2-hydroxy-4-acetoxy-6-methylbenzylidene)-(3-hydroxyphenyl)acetohydrazide (95), m.p. 203-205;
N-(2-hydroxy-4-bromobenzylidene)-(3-hydroxyphenyl)acetohydrazide (96), m.p. 204-205;
N-(3-chloro-4-hydroxybenzylidene)-(3-hydroxyphenyl)acetohydrazide (97), m.p. 209-210;
N-(2-hydroxy-3-bromo-5-methoxybenzylidene)-(3-hydroxyphenyl)acetohydrazide (98), m.p. 189-190;
N-(2,4,6-trimethylbenzylidene)-(3-hydroxyphenyl)acetohydrazide (99), m.p. 168-169;
N-(3,5-dibromo-4-hydroxybenzylidene)-(3-hydroxyphenyl)acetohydrazide (100), m.p. 236-237,
N-(4-hydroxy-3-nitrobenzylidene)-(3-hydroxyphenyl)acetohydrazide (101), m.p. 198;
N-(2,4,5-trimethoxybenzylidene)-(3-hydroxyphenyl)acetohydrazide (102), m.p. 235.5-236;
N-(2-methoxy-5-bromobenzylidene)-(3-hydroxyphenyl)acetohydrazide (103), m.p. 194-195;
N-(4-hydroxy-3-ethoxybenzylidene)-(3-hydroxyphenyl)acetohydrazide (104), m.p. 181.5;
N-(2-methoxy-4-nitrobenzylidene)-(3-hydroxyphenyl)acetohydrazide (105), m.p. 167-169;
N-(-(4-hydroxy-3-carboxybenzylidene)-3-hydroxyphenyl)acetohydrazide (106), m.p. 262-263 (decomposition);
N-(2-hydroxy-3-methoxy-5-bromobenzylidene)-(3-hydroxyphenyl)acetohydrazide (107), m.p. 177;
N-(4-carboxybenzylidene)-(3-hydroxyphenyl)acetohydrazide (108), m.p. 295-298 (decomposition);
N-(2,4-dimethylbenzylidene)-(3-hydroxyphenyl)acetohydrazide (109), m.p. 192.5;
N-(2-methylbenzylidene)-(3-hydroxyphenyl)acetohydrazide (110), m.p. 171-172;
N-(4-trifluoromethylbenzylidene)-(3-hydroxyphenyl)acetohydrazide (111), m.p. 201;
N-(4-trifluoromethoxybenzylidene)-(3-hydroxyphenyl)acetohydrazide (112), m.p. 175;
N-(2,4-dihydroxy-6-methylbenzylidene)-(3-hydroxy-5-methylphenyl)acetohydrazide (113), m.p. 152-156;
N-(2,4-dihydroxy-6-methylbenzylidene)-(3-hydroxy-2-methylphenyl)acetohydrazide (114), m.p. 225-227;
N-(2-hydroxy-4,6-dimethoxybenzylidene)-(3-hydroxyphenyl)acetohydrazide (115), m.p. 203-204.

The following examples relate to pharmaceutical compositions:

EXAMPLE A

Injection Vials

A solution of 100 g of an active ingredient according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient are introduced into hard gelatine capsules in a conventional manner in such a way that each capsule contains 20 mg of the active ingredient.

EXAMPLE H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

We claim:
1. A compound which is
N-(4-hydroxy-2-methoxybenzylidene)-(3-hydroxyphenyl)acetohydrazide,
N-[1-(4-hydroxy-2-methoxyphenyl)ethylidene]-(3-hydroxyphenyl)acetohydrazide,
N-(4-hydroxy-2-methoxybenzylidene)-(3-methoxyphenyl)acetohydrazide,
N-(3-fluoro-4-hydroxybenzylidene)phenylacetohydrazide,
N-(4-hydroxy-2-methoxybenzylidene)-(4-hydroxyphenyl)acetohydrazide,
N-(4-hydroxy-2-methoxybenzylidene)-(3,4-dichlorophenyl)acetohydrazide,

N-(4-hydroxy-2-methoxybenzylidene)-m-tolylacetohydrazide,
N-(4-hydroxy-2-methoxybenzylidene)-o-tolylacetohydrazide,
N-(4-hydroxy-2-methoxybenzylidene)-(2-chlorophenyl)acetohydrazide,
N-(4-hydroxy-2-methoxybenzylidene)-(3-chlorophenyl)acetohydrazide,
N-(4-hydroxy-2-methoxybenzylidene)-(4-fluorophenyl)acetohydrazide,
N-(4-hydroxy-2-methoxybenzylidene)-(2-chloro-4-fluorophenyl)acetohydrazide,
N-(4-hydroxy-2-methoxybenzylidene)-(3-fluorophenyl)acetohydrazide,
N-(4-hydroxybenzylidene)-(3-methoxyphenyl)acetohydrazide,
N-(4-hydroxy-2,6-dimethylbenzylidene)-(3-methoxyphenyl)acetohydrazide,
N-(3-fluoro-4-hydroxybenzylidene)-(3-methoxyphenyl)acetohydrazide,
N-[1-(4-hydroxy-2-methoxyphenyl)ethylidene]-(3-methoxyphenyl)acetohydrazide,
N-(4-hydroxy-2-methoxybenzylidene)-(3-methylsulfonyloxyphenyl)acetohydrazide,
N-(4-hydroxy-2-methoxybenzylidene)-(3,5-dihydroxyphenyl)acetohydrazide,
N-(3-fluoro-4-hydroxybenzylidene)-(3-fluorophenyl)acetohydrazide,
N-(4-acetoxy-2-methoxybenzylidene)-(3-methoxyphenyl)acetohydrazide,
N-(4-hydroxy-2-methoxybenzylidene)-(3-trifluoromethylphenyl)acetohydrazide,
N-(4-hydroxy-2-methoxybenzylidene)-3-(3-methoxyphenyl)propiohydrazide,
N-(2,4-dihydroxybenzylidene)-(3-methoxyphenyl)acetohydrazide,
N-(4-hydroxy-2-methoxybenzylidene)-(3-methoxyphenoxy)acetohydrazide,
N-(4-hydroxy-2-methoxybenzylidene)-(3-nitrophenyl)acetohydrazide,
N-(5-chloro-2-hydroxybenzylidene)-(3-methoxyphenyl)acetohydrazide,
N-(2-hydroxy-5-nitrobenzylidene)-(3-methoxyphenyl)acetohydrazide,
N-(4-hydroxy-2-methoxybenzylidene)-2-hydroxy-2-phenylacetohydrazide,
N-(2-ethoxy-4-hydroxybenzylidene)-(3-methoxyphenyl)acetohydrazide,
N-(4-hydroxy-2-methoxybenzylidene)-(3-bromophenyl)acetohydrazide,
N-[1-(4-hydroxyphenyl)ethylidene]-(3-methoxyphenyl)acetohydrazide,
N-(4-hydroxy-2-methoxybenzylidene)-(3,5-difluorophenyl)acetohydrazide,
N-(4-hydroxy-2-methylbenzylidene)-(3-hydroxyphenyl)acetohydrazide,
N-(2-ethoxy-4-hydroxybenzylidene)-(3-hydroxyphenyl)acetohydrazide,
N-(2-methoxy-4-hydroxy-6-methylbenzylidene)-(3-hydroxyphenyl)acetohydrazide,
N-(2-methoxy-4-hydroxybenzylidene)-(2-fluorophenyl)acetohydrazide,
N-(2,4-dihydroxybenzylidene)-(3-hydroxyphenyl)acetohydrazide,
N-(2-hydroxy-5-chlorobenzylidene)-(3-hydroxyphenyl)acetohydrazide,
N-(4-methylsulfonylbenzylidene)-(3-hydroxyphenyl)acetohydrazide,
N-(2,6-dimethyl-4-hydroxybenzylidene)-(3-hydroxyphenyl)acetohydrazide,
N-(2-methoxy-4-hydroxybenzylidene)-(3-hydroxy-4-methoxyphenyl)acetohydrazide,
N-(2-methoxy-4-hydroxybenzylidene)-(2,3-dimethoxyphenyl)acetohydrazide,
N-(2-methoxy-4-hydroxybenzylidene)-(3-aminophenyl)acetohydrazide,
N-(2,4-dihydroxy-6-methylbenzylidene)-(3-hydroxyphenyl)acetohydrazide,
N-(2-methoxy-4-hydroxybenzylidene)-(2-methyl-3-methoxyphenyl)acetohydrazide,
N-(4-bromobenzylidene)-(3-hydroxyphenyl)acetohydrazide,
N-(4-iodobenzylidene)-(3-hydroxyphenyl)acetohydrazide,
N-(2-hydroxy-3-bromo-5-chlorobenzylidene)-(3-hydroxyphenyl)acetohydrazide,
N-(2-hydroxy-5-tert-butylbenzylidene)-(3-hydroxyphenyl)acetohydrazide,
N-(2-hydroxy-5-bromobenzylidene)-(3-hydroxyphenyl)acetohydrazide,
N-(2-hydroxy-5-trifluoromethoxybenzylidene)-(3-hydroxyphenyl)acetohydrazide,
N-(2-hydroxy-3-methoxy-5-nitrobenzylidene)-(3-hydroxyphenyl)acetohydrazide,
N-(4-hydroxybenzylidene)-(3-hydroxyphenyl)acetohydrazide,
N-(4-hydroxy-2-methoxybenzylidene)-(3-ethoxyphenyl)acetohydrazide,
N-(2-hydroxy-3,5-dichlorobenzylidene)-(3-hydroxyphenyl)acetohydrazide,
N-(2-hydroxy-5-iodobenzylidene)-(3-hydroxyphenyl)acetohydrazide,
N-(2-hydroxy-3-methyl-5-chlorobenzylidene)-(3-hydroxyphenyl)acetohydrazide,
N-(2-hydroxy-5-fluorobenzylidene)-(3-hydroxyphenyl)acetohydrazide,
N-(2-hydroxy-6-methylbenzylidene)-(3,5-difluorophenyl)acetohydrazide,
N-(2-hydroxy-6-methylbenzylidene)-(3-fluorophenyl)acetohydrazide,
N-(2-hydroxy-6-methylbenzylidene)phenyl acetohydrazide,
N-[1-(4-hydroxyphenyl)ethylidene]-(3-hydroxyphenyl)acetohydrazide,
N-[1-(2,4-dihydroxyphenyl)ethylidene]-(3-hydroxyphenyl)acetohydrazide,
N-(2,4-dihydroxy-6-methylbenzylidene)-(3-methyl-5-methoxyphenyl)acetohydrazide,
N-(2,4-dihydroxy-6-methylbenzylidene)-(3,5-dihydroxyphenyl)acetohydrazide,
N-(2-hydroxy-4-carboxybenzylidene)-(3-hydroxyphenyl)acetohydrazide,
N-(2,3-dimethyl-4-hydroxybenzylidene)-(3-hydroxyphenyl)acetohydrazide,
N-(3,5-di-tert-butyl-4-hydroxybenzylidene)-(3-hydroxyphenyl)acetohydrazide,
N-(3,5-dimethyl-4-hydroxybenzylidene)-(3-hydroxyphenyl)acetohydrazide,
N-(2-acetoxybenzylidene)-(3-hydroxyphenyl)acetohydrazide,
N-(2-hydroxybenzylidene)-(3-hydroxyphenyl)acetohydrazide, N-(2-hydroxy-3-methoxybenzylidene)-(3-hydroxyphenyl)acetohydrazide,
N-(2-hydroxy-5-methoxybenzylidene)-(3-hydroxyphenyl)acetohydrazide,
N-(2-hydroxy-5-nitrobenzylidene)-(3-hydroxyphenyl)acetohydrazide,
N-(2-hydroxy-3-methylbenzylidene)-(3-hydroxyphenyl)acetohydrazide,
N-(2-hydroxy-3-nitrobenzylidene)-(3-hydroxyphenyl)acetohydrazide,
N-(2-hydroxy-6-methoxybenzylidene)-(3-hydroxyphenyl)acetohydrazide,
N-(2-hydroxy-5-methylbenzylidene)-(3-hydroxyphenyl)acetohydrazide,
N-(3-bromobenzylidene)-(3-hydroxyphenyl)acetohydrazide,
N-(2-hydroxy-3-tert-butylbenzylidene)-(3-hydroxyphenyl)acetohydrazide,
N-(2-hydroxy-4-methylbenzylidene)-(3-hydroxyphenyl)acetohydrazide,
N-(2-hydroxy-3-nitro-5-bromobenzylidene)-(3-hydroxyphenyl)acetohydrazide,
N-(2-hydroxy-4-methyl-5-chlorobenzylidene)-(3-hydroxyphenyl)acetohydrazide,
N-(2,6-dimethoxybenzylidene)-(3-hydroxyphenyl)acetohydrazide,
N-(2-hydroxy-3-fluorobenzylidene)-(3-hydroxyphenyl)acetohydrazide,
N-(2-hydroxy-3-bromo-5-nitrobenzylidene)-(3-hydroxyphenyl)acetohydrazide,
N-(2-hydroxy-6-methylbenzylidene)-(3-hydroxyphenyl)acetohydrazide,
N-(2-hydroxy-4-methoxy-6-methylbenzylidene)-(3-hydroxyphenyl)acetohydrazide,
N-(2-hydroxy-4-acetoxy-6-methylbenzylidene)-(3-hydroxyphenyl)acetohydrazide,
N-(2-hydroxy-4-bromobenzylidene)-(3-hydroxyphenyl)acetohydrazide,
N-(3-chloro-4-hydroxybenzylidene)-(3-hydroxyphenyl)acetohydrazide,
N-(2-hydroxy-3-bromo-5-methoxybenzylidene)-(3-hydroxyphenyl)acetohydrazide,
N-(2,4,6-trimethylbenzylidene)-(3-hydroxyphenyl)acetohydrazide,
N-(3,5-dibromo-4-hydroxybenzylidene)-(3-hydroxyphenyl)acetohydrazide,
N-(2,4,5-trimethoxybenzylidene)-(3-hydroxyphenyl)acetohydrazide,
N-(2-methoxy-5-bromobenzylidene)-(3-hydroxyphenyl)acetohydrazide,
N-(4-hydroxy-3-ethoxybenzylidene)-(3-hydroxyphenyl)acetohydrazide,
N-(2-methoxy-4-nitrobenzylidene)-(3-hydroxyphenyl)acetohydrazide,
N-(-(4-hydroxy-3-carboxybenzylidene)-3-hydroxyphenyl)acetohydrazide,
N-(2-hydroxy-3-methoxy-5-bromobenzylidene)-(3-hydroxyphenyl)acetohydrazide,
N-(4-carboxybenzylidene)-(3-hydroxyphenyl)acetohydrazide,
N-(2,4-dimethylbenzylidene)-(3-hydroxyphenyl)acetohydrazide,
N-(2-methylbenzylidene)-(3-hydroxyphenyl)acetohydrazide,
N-(4-trifluoromethylbenzylidene)-(3-hydroxyphenyl)acetohydrazide,
N-(4-trifluoromethoxybenzylidene)-(3-hydroxyphenyl)acetohydrazide,
N-(2,4-dihydroxy-6-methylbenzylidene)-(3-hydroxy-5-methylphenyl)acetohydrazide,
N-(2,4-dihydroxy-6-methylbenzylidene)-(3-hydroxy-2-methylphenyl)acetohydrazide, or
N-(2-hydroxy-4,6-dimethoxybenzylidene)-(3-hydroxyphenyl)acetohydrazide,
or a pharmaceutically acceptable prodrug, salt, or stereoisomer thereof or a mixture thereof in all ratios.

2. A pharmaceutical composition comprising at least one compound according to claim 1 and pharmaceutically acceptable cater or vehicle.

3. A kit comprising
  (a) a first package comprising a compound according to claim 1 or a pharmaceutical composition thereof, and
  (b) a second package comprising an effective amount of a further medicament active ingredient.

4. A compound of claim 1 which is in E stereoisomer configuration.

5. A prodrug compound of claim 1 which comprises a cleavable alkyl, acyl, sugar or oligopeptide group or a biodegradable polymer.

* * * * *

UNITED STATES PATENT AND TRADEMARK OFFICE
CERTIFICATE OF CORRECTION

| | |
|---|---|
| PATENT NO. | : 7,405,239 B2 |
| APPLICATION NO. | : 10/574781 |
| DATED | : July 29, 2008 |
| INVENTOR(S) | : Rolf Gericke |

It is certified that error appears in the above-identified patent and that said Letters Patent is hereby corrected as shown below:

Column 32, line 34 reads "cater." should read --carrier.--

Signed and Sealed this

Twenty-first Day of October, 2008

JON W. DUDAS
*Director of the United States Patent and Trademark Office*